United States Patent
Oishi et al.

[11] 3,966,789
[45] June 29, 1976

[54] N-SUBSTITUTED AMINONITRILE DERIVATIVES

[75] Inventors: Tadashi Oishi; Nobuyuki Kameda; Toshiro Kato; Akira Fujinami, all of Hyogo; Toshiaki Ozaki, Osaka; Eiyashi Itooka, Hyogo, all of Japan

[73] Assignee: Sumitomo Chemical Company, Limited, Osaka, Japan

[22] Filed: Sept. 5, 1974

[21] Appl. No.: 503,425

[30] Foreign Application Priority Data
Sept. 5, 1973   Japan.............................. 48-100547

[52] U.S. Cl............................ 260/465.4; 260/404.5; 260/465.5 R; 424/304
[51] Int. Cl.$^2$................................. C07C 121/417
[58] Field of Search..................... 260/465.4, 404.5

[56] References Cited
UNITED STATES PATENTS

| | | | |
|---|---|---|---|
| 2,479,942 | 8/1949 | Lecher et al................. | 260/465.5 R |
| 2,585,988 | 2/1952 | Asscher....................... | 260/570.6 |
| 2,810,675 | 10/1957 | de Benneville et al........... | 424/304 |
| 3,102,068 | 8/1963 | Tolbert......................... | 260/465.4 X |
| 3,247,206 | 4/1966 | Yost et al..................... | 260/465.4 X |
| 3,655,684 | 4/1972 | Osbond et al................. | 260/465.4 X |

FOREIGN PATENTS OR APPLICATIONS

2,033,393   1/1971   Germany...................... 260/465.5 R

OTHER PUBLICATIONS

Exner et al., J.A.C.S., 75, (1953), pp. 4841–4842.
Tiollais, Bull. Soc. Chem., France, (1947), pp. 959–968.

*Primary Examiner*—Joseph Paul Brust
*Attorney, Agent, or Firm*—Sughrue, Rothwell, Mion, Zinn & Macpeak

[57] ABSTRACT

N-substituted aminonitrile derivatives of the formula (I)

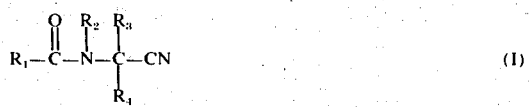

wherein $R_1$, $R_2$, $R_3$ and $R_4$ are as hereinafter defined, useful as fungicides, method for their preparation, and fungicidal compositions containing the N-substituted aminonitrile derivatives of the formula (I).

1 Claim, No Drawings

N-SUBSTITUTED AMINONITRILE DERIVATIVES

BACKGROUND OF THE INVENTION

The present invention relates to cyano compounds, a process for preparing the cyano compounds, and fungicidal compositions containing the cyano compounds.

SUMMARY OF THE INVENTION

An object of the present invention is to provide fungicidally advantageous cyano compounds of the formula (I) having excellent low-toxicity to warm-blooded animals. The present invention pertains to cyano compounds represented by the formula (I),

wherein $R_1$ represents a $(C_2-C_{20})$ alkyl group, or a halogen-substituted $(C_2-C_{20})$ alkyl group; $R_2$ represents a $(C_2-C_5)$ alkenyl group, a $(C_2-C_5)$ haloalkenyl group or a $(C_2-C_5)$ alkynyl group; and $R_3$ and $R_4$ each represents a hydrogen atom or a $(C_1-C_4)$ alkyl group.

DETAILED DESCRIPTION OF THE INVENTION

The compounds according to the present invention of the formula (I) can be prepared by the following methods.

The N-substituted aminonitrile derivatives of the formula (I) can be prepared by reacting an acyl chloride derivative of the formula (II)

wherein $R_1$ is the same defined above, with a glycinonitrile derivative of the formula (III),

wherein $R_2$, $R_3$ and $R_4$ are the same as defined above, in the presence of a suitable tertiary amine.

The above described method is illustrated below in greater detail.

Generally, 0.1 mole of the glycinonitrile derivative of the formula (III), 0.11 mole of a suitable tertiary amine such as, for example, triethylamine, pyridine, N,N-dimethylaniline, N,N-diethylaniline or N-methylmorpholine, and with triethylamine being preferred, and an appropriate amount of a suitable inert solvent such as, for example, benzene, toluene, diethyl ether, isopropyl ether, tetrahydrofuran, dioxane, acetone, methyl isobutyl ketone or ethyl acetate, with toluene being preferred, are placed in a four-neck flask, and then 0.1 mole of an acyl chloride of the formula (II) is gradually added dropwise thereto, while stirring, within a temperature range of about 0°C to about the boiling point of the solvent. After the addition, stirring is continued for some time to ensure completion of the reaction. Thereafter, the reaction solution is cooled, washed successively with water, an aqueous dilute alkaline solution and an aqueous dilute material acid solution, and then the separated organic layer is dried over a suitable drying agent, such as, for example, calcium chloride, anhydrous sodium sulfate or anhydrous magnesium sulfate, and the solvent evaporated under reduced pressure. The resulting residue is distilled under reduced pressure to obtain the desired N-acylglycinonitrile derivatives in a pure form and in a high yield.

The starting materials of the present invention, a glycinonitrile derivative of the formula (III), can be prepared, for example, by reacting an amine of the formula (IV),

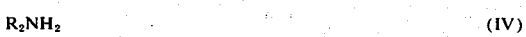

wherein $R_2$ has the same meaning as defined above, with a carbonyl compound of the formula (V),

wherein $R_3$ and $R_4$ have the same meanings as defined above, to produce a Schiff base of the formula (VI),

wherein $R_2$, $R_3$ and $R_4$ have the same meanings as defined above, and then by adding hydrogen cyanide to the resulting Schiff base. The method is illustrated in greater detail as follows. Generally, 1 mole of the carbonyl compound of the formula (V) is first dissolved in a suitable solvent, such as, for example, water, an alcohol, ethyl acetate, dioxane, tetrahydrofuran, dimethylsulfoxide, dimethylformamide or ligroin, with water being preferred, and then gradually stirred into 1.2 moles of the amine of the formula (IV) in the presence of or absence of sodium hydrogen sulfite, while cooling or heating, if desired.

Thereafter, an aqueous solution containing 1 mole of potassium cyanide is added to the resulting solution and stirring is continued. After completion of the reaction, the reaction solution is allowed to stand and the separated oily layer is dried to obtain the desired N-substituted aminonitrile derivatives in a pure form and in a high yield. The product thus obtained can be further purified by distillation under reduced pressure, if desired.

The following compounds are specific examples of compounds according to the present invention which are given only for the purpose of illustration. The invention is not to be interpreted as being limiting thereto. As a matter of course, the present invention includes various isomeric forms including optical isomers.

Table 1

| Compound No. | Compounds | Properties |
|---|---|---|
| (1) | ClCH$_2$CH$_2$CH$_2$C(=O)N(CH$_2$CH=CH$_2$)(CH$_2$CN) | $n_D^{22.5}$ 1.4952 |

Table 1-continued

| Compound No. | Compounds | Properties |
|---|---|---|
| (2) | ClCH$_2$CH$_2$CH$_2$C(=O)N(CH$_2$CH=CHCH$_3$)(CH$_2$CN) | $n_D^{23.0}$ 1.4926 |
| (3) | ClCH$_2$CH$_2$CH$_2$C(=O)N(CH$_2$CH=CH$_2$)(CH(CH$_3$)CN) | $n_D^{25.5}$ 1.4882 |
| (4) | ClCH$_2$CH$_2$CH$_2$C(=O)N(CH$_2$CH=CH$_2$)(C(CH$_3$)$_2$CN) | $n_D^{26.0}$ 1.4915 |
| (5) | ClCH$_2$CH$_2$CH$_2$C(=O)N(CH$_2$CH=CH$_2$)(CH$_2$CH$_2$CN) | $n_D^{23.0}$ 1.4932 |
| (6) | C$_2$H$_5$C(=O)N(CH$_2$CH=CH$_2$)(CH$_2$CN) | $n_D^{20.5}$ 1.4722 |
| (7) | n-C$_3$H$_7$C(=O)N(CH$_2$CH=CH$_2$)(CH$_2$CN) | $n_D^{22.0}$ 1.4690 |
| (8) | (CH$_3$)$_2$CHC(=O)N(CH$_2$CH=CH$_2$)(CH$_2$CN) | $n_D^{24.7}$ 1.4709 |
| (9) | n-C$_5$H$_{11}$C(=O)N(CH$_2$CH=CH$_2$)(CH$_2$CN) | $n_D^{28.0}$ 1.4662 |
| (10) | n-C$_{11}$H$_{23}$C(=O)N(CH$_2$CH=CH$_2$)(CH$_2$CN) | $n_D^{27.5}$ 1.4670 |
| (11) | n-C$_{17}$H$_{35}$C(=O)N(CH$_2$CH=CH$_2$)(CH$_2$CN) | m.p. 54.5–55.0°C |
| (12) | CH$_3$CH$_2$CHCl-C(=O)N(CH$_2$CH=CH$_2$)(CH$_2$CN) | $n_D^{24.5}$ 1.4872 |
| (13) | ClCH$_2$CH$_2$C(=O)N(CH$_2$CH=CH$_2$)(CH$_2$CN) | $n_D^{22.5}$ 1.4978 |
| (14) | CH$_3$CHCl-C(=O)N(CH$_2$CH=CH$_2$)(CH$_2$CN) | $n_D^{22.5}$ 1.4915 |
| (15) | n-C$_7$H$_{15}$C(=O)N(CH$_2$CH=CH$_2$)(CH$_2$CN) | $n_D^{27.5}$ 1.4699; b.p.$_{0.2 mm}$ 131–138.5°C |

Table 1-continued

| Compound No. | Compounds | Properties |
|---|---|---|
| (16) | n-$C_{15}H_{31}$C(=O)N(CH$_2$CH=CH$_2$)(CH$_2$CN) | m.p. 50.0–51.0°C |
| (17) | $CH_3$CHCH$_2$C(=O)N(CH$_2$CH=CH$_2$)(CH$_2$CN), Cl | $n_D^{27.0}$ 1.4889; b.p.$_{0.15}$ 112–116°C |
| (18) | $CH_3$C(Cl)(Cl)C(=O)N(CH$_2$CH=CH$_2$)(CH$_2$CN) | $n_D^{27.5}$ 1.4892; b.p.$_{0.13}$ 80–82°C |
| (19) | $CH_3CH_2CH_2$CH(Br)C(=O)N(CH$_2$CH=CH$_2$)(CH$_2$CN) | $n_D^{27.5}$ 1.4972; b.p.$_{0.12}$ 108–109°C |
| (20) | BrCH$_2$CH$_2$C(=O)N(CH$_2$CH=CH$_2$)(CH$_2$CN) | $n_D^{27.0}$ 1.5140; b.p.$_{0.12}$ 123–128°C |
| (21) | Cl(H)C=CH—CH$_2$—N(C(=O)(CH$_2$)$_2$CH$_3$)(CH$_2$CN) | $n_D^{26.0}$ 1.4975 |
| (22) | HC≡C—CH$_2$N(C(=O)(CH$_2$)$_2$CH$_2$Cl)(CH$_2$CN) | $n_D^{27.5}$ 1.4988 |

The following are typical examples of acylchlorides of the formula (V) which are, needless to say, only given for illustration and are not to be interpreted as limiting the invention.

Acylchlorides $C_2H_5$COCl
$C_3H_7$COCl (straight or branched chain)
$C_4H_9$COCl (straight or branched chain)
$C_5H_{11}$COCl (straight or branched chain)
$C_6H_{13}$COCl (straight or branched chain)
$C_8H_{17}$COCl (straight or branched chain)
$C_{10}H_{21}$COCl (straight or branched chain)
$C_{14}H_{29}$COCl (straight or branched chain)
$C_{16}H_{33}$COCl (straight or branched chain)
Cl—CH$_2$—CH$_2$COCl
Br—CH$_2$—CH$_2$—COCl
CH$_3$—CHBr—COCl
CH$_3$—C(Br$_2$)—COCl
Cl—CH$_2$—CHCl—COCl
Cl—CH$_2$—CH$_2$—CH$_2$—COCl
CH$_3$—CHCl—CH$_2$—COCl
CH$_3$—CH$_2$—CHCl—COCl
Br—CH$_2$—CH$_2$—CH$_2$—COCl
CH$_3$—CH$_2$—CHBr-COCl
Cl$_2$CH—CH$_2$—CH$_2$—COCl
ClCH$_2$—CH$_2$—CH$_2$—CH$_2$—COCl
ClCH$_2$—(CH$_2$)$_{10}$—COCl Although many N-substituted aminonitrile derivatives are well known, the present compounds are all new aminonitrile derivatives and they have a broad and strong fungicidal activity which would not be expected from other homologues, as disclosed in Helv. Chim. Acta., 44, 1237, (1961); U.S. Pat. Nos. 3,174,975 and 3,202,674; Monatsh, 93, 469, (1962), and so on.

That is, the compounds of formula (I) in which $R_1$ is a halomethyl group have a strong herbicidal activity, however, it is surprising that, when $R_1$ is a haloalkyl group in which the alkyl moiety is an ethyl or higher alkyl moiety, the herbicidal activity completely disappears while the fungicidal activity becomes strong. Such a unique biological activity was first discovered in the present invention and the present invention was completed on the basis of this finding.

An object of the present invention is the control of pathogenic microorganisms and protection of plants and animals other than humans and various materials from microorganisms. In the first place, the N-acylglycinonitrile derivatives of the formula (I) are chemicals suitable for controlling plant diseases, and they have an extremely high controlling effect on plant diseases due to soil pathogens, for example, fusarium wilt of the tomato (*Fusarium oxysporum f. lycopersici*), yellows of the Japanese radish (*Fusarium oxysporum f. raphani*), fusarium wilt of the cucumber (*Fusarium oxysporum f. cucumerinum*), verticillium wilt of the eggplant (*Verticillium albo-atrum*), yellows of the strawberry (*Fusarium oxysporum*), fusarium wilt of cotton (*Fusarium oxysporum f. vasinfectum*), damping-off of vegetables (*Pythium spp.*), southern blight of vegetables (*Corticium rolfsii*), damping-off of vegetables (*Rhizoctonia solani*) and violet root rot of the sweet potato (*Helicobasidium mompa*). In addition, the N-acylglycinonitrile derivatives have also a high controlling effect on plant diseases such as rice blast (*Pyricularia oryzae*), helminthosporium leaf spot of rice (*Cochliobolus miyabeanus*), sheath blight of rice (*Pellicularia sasakii*), bacterial leaf blight of rice (*Xanthomonas oryzae*), stem rot of rice (*Helminthosporium sigmoideum*), 'bankanae' disease of rice (*Gibberella fujikuroi*), rust of cereals (*Puccinia spp.*), smut of cereals (*Ustilago spp.*), powdery mildew of vegetables and cereals (*Sphaerotheca fuliginea* and *Erysiphe graminis*), downy mildew of vegetables and fruit trees (*Pseudoperonospora spp.* and *Plasmopara spp.*), late blight of vegetables and the potato (*Phytophthora infestans*), anthracnose of vegetables and fruit trees (*Colletotrichum spp.* and *Gloeosporium spp.*), stem rot of vegetables and beans (*Sclerotinia spp.*), gray mold of vegetables (*Botrytis spp.*), brown rot of the peach (*Sclerotinia cinerea*), ripe rot of the grape (*Glomerella cingulata*), rust of the grape (*Phakopsora ampelopsidis*), black spot of the pear (*Alternaria kikuchiana*), alternaria leaf spot of the apple (*Alterneria mali*), apple scab (*Venturia insequalis*), blossom blight of the apple (*Sclerotinia mali*), citrus scab (*Elsinoe fawcetti*) and so on. As set forth above, the compounds according to the present invention have an excellent controlling effect on plant diseases.

Secondly, as the result of continued study, it has been surprisingly found that the compounds according to the present invention also show a strong antimicrobial activity on microorganisms other than plant pathogens. That is, the present compounds can be used not only as detergents for wood-, bamboo-, fiber- and paper-products; antimicrobial additives or antiseptic agents for industrial products such as cosmetics, glasses, paints and synthetic resins, but also as slime controlling agents. These fields are completely different fields of application from agricultural and horticultural applications. Therefore, the microorganisms involved are different from plant pathogens and the method of application is also different from the method of application in agriculture and horticulture.

Furthermore, the compounds of the present invention are much superior, in addition to their wide spectrum of fungicidal activity as described above, in that they are very low in toxicity to warm-blooded animals and do not irritate the skin at the concentrations practically applied.

The compounds of the present invention have a fungicidal activity to both gram positive and gram negative bacteria. Another advantageous property of the present compounds is that they are completely or almost colorless. This property allows the compounds of the present invention to be used for purposes for which highly colored, well-known compounds could not be used.

The compounds of the present invention can directly be incorporated in the materials to be protected, for example fiber-products (particularly blended yarns of cellulose or viscose), materials containing synthetic resin substrates such as a polyamide or polyvinyl chloride, casein-containing paints or lacquers, inorganic or organic pigments, thickening agents made from starch or cellulose derivatives, oils, materials containing polyvinyl alcohol as a substrate for achieving permanent press characteristics in fabrics, cosmetics such as soaps or creams, ointments, powders or tooth-powders. In addition to the above direct incorporation, the compounds of the present invention can also be used in the form of an aerosol, an organic solution as impregnates for wood and an emulsified solution.

Furthermore, the compounds according to the present invention can be used, in the form of an aqueous suspension, for protecting substances which easily rot, for example, leather and paper, together with wetting agents or dispersing agents. The preferred use of the compounds of the invention is disinfection of washed products and protection of the products from microorganisms. For this purpose the compounds of the present invention are preferably used in the form of a liquid composition containing 0.1 to 500 ppm of the compounds. However, concentrations outside this range can be employed where desired.

The compounds of the present invention are soluble in most organic solvents, regardless of whether the solvent is hydrophilic or hydrophobic, such as, for example, benzene, xylene, diethyl ether, dioxane, acetone, methyl isobutyl ketone, cyclohexanone, isophorone, chloroform, trichloroethane, methylcellosolve, ethylcellosolve, butylcellosolve, dimethylformamide, dimethylsulfoxide. acetonitrile and methylnaphthalene.

In practical application of the compounds of the present invention, they can be used alone without adding any other components, or can be used in combination with carriers which facilitate their application. For example as pesticides, they can be used in common preparation forms such as dusts, wettable powders, emulsifiable concentrates, granules, oil sprays, aerosols, fine granules and fumigants.

The carriers used can be solids, liquids or gases. Examples of solid carriers include clay, talc, diatomaceous earth, bentonite, kaolin, terra abla and vermiculite. Examples of liquid carriers include water, alcohols, ketones, benzene, xylene, toluene, solvent naphtha, petroleum ether and kerosene. Examples of gaseous carriers include Freon, deodorized liquified petroleum gas, methyl chloride, vinyl chloride monomer, dimethyl ether, nitrogen and carbon dioxide. These preparations can be applied by spraying, dusting or injection in the form of an aqueous solution or without dilution.

Furthermore, the compounds according to the present invention can be employed in combination with other chemicals, for example Blasticidin-S, Kasugamycin, Polyoxin, Validamycin, Cellocidin, 3-[2-(3,5-dimethyl-2-oxocyclohexyl)-2-hydroxyethyl]-glutarimide, Streptomycin, Griseofulvin, pentachloronitrobenzene, pentachlorophenol, hexachlorobenzene, trichloronitromethane, 1,1,1-trichloro-2-nitroethane, dichlorodinitromethane, trichloronitroethylene, 1,1,2,2-tetrachloronitroethane, methylene-bis-thiocyanate, 2,6-dichloro-4-nitroaniline, zinc ethylene-bis-dithiocarbamate, zinc dimethyldithiocarbamate, manganous ethylene-bis-dithiocarbamate, bis-(dimethylthiocarbamoyl)-disulfide, 2,4,5,6-tetrachloro-isophthalonitrile, 2,3-dichloro-1,4-naphthoquinone, tetrachloro-p-benzoquinone, p-dimethylaminobenzene diazo sodium sulfonate, 2-(1-methylheptyl)-4,6-dinitrophenylcrotonate, 2-heptadecylimidazoline acetate, 2,4-dichloro-6-(o-chloroanilino)-S-triazine, dodecylguanidine acetate, 6-methyl-2,3-quinoxaline-dithiol cyclic-S,S-dithiocarbonate, 2,3-quinoxaline-dithiol cyclic trithiocarbonate, N-trichloromethylthio-4-cyclohexene-1,2-dicarboxyimide, N-(1,1,2,2-tetrachloroethylthio)-4-cyclohexene-1,2-dicarboxyimide, N-(dichlorofluoromethylthio)-N-(dimethylsulfamoyl)-aniline, 1,2-bis-(3-methoxycarbonyl-2-thioureido)- benzene, 1,2-bis-(3-ethoxycarbonyl-2-thioureido)-benzene, 2-amino-1,3,4-thiadiazole, 2-amino-5-mercapto-1,3,4-thiadiazole, o-phenylphenol, N-(3',5'-dichlorophenyl)-maleimide, N-(3',5'-dichlorophenyl)-succinimide, N-(3',5'-dichlorophenyl)-itaconimide, 3-(3',5'-dichlorophenyl)-5,5-dimethyloxazoline-2,4-dione, 2,3-dihydro-5-carboxanilide-6-methyl-1,4-oxathiine-4,4-dioxide, 2,3-dihydro-5-carboxanilide-6-methyl-1,4-oxathiine, 1-(N-n-butylcarbamoyl)-2methoxycarbonylaminobenzimidazole, O,O-diisopropyl-S-benzyl-phosphorothioate, O-ethyl-S,S-diphenylphosphorodithioate, O-butyl-S-benzyl-S-ethylphosphorodithioate, O-ethyl-O-phenyl-O-(2,4,5-trichlorophenyl)phosphate, O,O-dimethyl-O-(3-methyl-4-nitrophenyl)phosphorothioate, S-[1,2,-bis(ethoxycarbonyl)-ethyl]-O,O-dimethylphosphorodithioate, O,O-dimethyl-S-(N-methylcarbamoylmethyl)phosphorodithioate, O,O-diethyl-O-(2-isopropyl-6-methyl-4-pyrimidyl)thiophosphate, 3,4-dimethylphenyl-N-methylcarbamate, iron methanearsonate, ammonium iron methanearsonate, 2-chloro-4,6-bis-(ethylamino)-S-triazine, 2,4-dichlorophenoxyacetic acid (including the salts and esters thereof), 2-methyl-4-chlorophenoxyacetic acid (including the salts and esters thereof), 2,4,6-trichlorophenyl-4'-nitrophenyl ether, sodium pentachlorophenolate, N-(3,4-dichlorophenyl)propionamide, 3-(3',4'-dichlorophenyl)-1,1-dimethylurea, α,α,α-trifluoro-2,6-dinitro-N,N-di-n-propyl-p-toluidine, 2-chloro-2',6'-diethyl-N-(methoxymethyl)acetamide, 1-naphthyl-N-methylcarbamate, methyl-N-(3,4-dichlorophenyl)-carbamate, 4-chlorobenzyl-N,N-dimethylthiocarbamate, N,N-diallyl-2-chloroacetamide, O-ethyl-O-(3-methyl-6-nitrophenyl)-N-sec.-butylphosphorothioamidate, S-n-butyl-S-(p-tert.-butylbenzyl)-N-(3-pyridyl)imidodithiocarbonate, S-n-heptyl-S'-(p-tert.-butylbenzyl)-N-(3-pyridyl)imidodithiocarbonate, 5-ethoxy-3-trichloromethyl-1,2,4-thiadiazole and 3-hydroxy-5-methylisooxazole.

In these cases, since the controlling effect of each active ingredient in the mixed preparations is not affected, a simultaneous controlling effect on more than two kinds of pathogenic oganisins can be obtained, and furthermore a synergistic effect is observed with some combinations which is particularly advantageous in practical application. The compounds of the invention can also be used in combination with agricultural chemicals such as fungicides, nematocides and acaricides, or with fertilizers.

For industrial use, the compounds of the invention can be applied in a pure form which does not contain any other inert component. Alternatively, they can be applied by formulation into suitable preparation forms with other inert components (e.g., carriers), for example, into a liquid form since the compounds of the invention are very soluble in most organic solvents, and then by mixing with industrial products or by coating, injection or dipping as the need arises.

The preparation of the compounds of the present invention is specifically illustrated with reference to the following examples, which are only given for the purpose of illustration and the invention is not to be interpreted as being limited to these Examples. Unless otherwise indicated, all parts, percents, ratios and the like are by weight.

EXAMPLE 1

4.8g of N-allyl-glycinonitrile, 5.6g of triethylamine and 50 ml of toluene were placed in a four-neck 100ml-flask, and 7.1g of 4-chloro-butyryl-chloride was gradually added dropwise thereto at room temperature while stirring. After stirring at 60°C for 1 hour, the reation solution was cooled and successively washed with water, with a 5% aqueous sodium hydroxide solution and with a 5% aqueous hydrochloric acid solution. The separated toluene layer was dried over anhydrous sodium sulfate and distilled under reduced pressure to remove the toluene. The residual solution was vacuum distilled to obtain 9.4g of the desired 4-chloro-N-cyanomethyl-N-allylbutyrylamide (b.p.$_2$ 145° – 148°C, $n_D^{23}$ 1.4952).

Elemental Analysis:

|  | C | H | N | Cl |
|---|---|---|---|---|
| Calculated (%) (as $C_9H_{13}N_2OCl$) | 53.87 | 6.53 | 13.96 | 17.67 |
| Found (%) | 53.63 | 6.58 | 13.70 | 17.39 |

FORMULATON EXAMPLES

1. Dust

Two parts by weight of Compounds (1) and (7), and 98 parts of clay were well mixed while powdering to obtain two dusts containing 2% of the active ingredient. Application of the dusts can be by dusting as they are.

2. Wettable powder

Fifty parts by weight of Compound (14), 5 parts of a wetting agent (an alkylbenzene sulfonate) and 45 parts of diatomaceous earth were well mixed while powdering to obtain a wettable powder containing 50% of the active ingredient. Application of the powder can be by spraying in the form of an aqueous dilute solution.

3. Emulsifiable concentrate

Fifty parts by weight of Compound (20), 35 parts of xylene and 15 parts of an emulsifier (a polyoxyethylenephenylphenol polymer) were well mixed to obtain an emulsifiable concentrate containing 50% of the active ingredient. Application can be by spraying in the form of an aqueous dilute solution.

4. Granules

Five parts by weight of Compound (2), 90 parts of silica powder, 4.95 parts of calcium lignosulfonate and 0.05 part of sodium alkylbenzene sulfonate were well mixed while powdering, kneaded well with water, granulated and dried to obtain a granular product containing 5% of the active ingredient. Application of the granular product can be as it is on or in water, or on or in soil.

5. Oil spray 0.5 part by weight of Compound (4) was well mixed with 99.5 parts of kerosene to obtain an oil spray containing 0.5% of the active ingredient. Application of the oil spray can be by spraying, injection or in the form of an aerosol.

The biological activity of the present compounds is illustrated below by reference to the following examples which are only given for purpose of illustration and the invention is not to be interpreted as being limiting thereto.

TEST EXAMPLE 1

Protective Activity on Yellows of the Japanese Radish (*Fusarium oxysporum f. raphania*)

A plastic vat of an area of 0.1 m² was filled with field soil, which was then mixed with soil infested with *Fu-* sarium oxysporum f. raphania to a depth of 5 cm from the soil surface. Radish seeds (var.: Wase-40 nichi) were sowed on the surface at a rate of 50 per vat and covered with soil. Then an aqueous solution of each emulsifiable concentrate of compounds of the present invention was applied at a rate of 300 ml per vat. After greenhouse-cultivation for one month, the disease severity was checked and the percentage of healthy seedlings was calculated according to the following relationship.

$$\text{Percentage of Healthy Seedlings} = \frac{\text{Number of Healthy Seedlings in Each Treated Plot}}{\text{Number of Germinations in an Untreated and Uninoculated Plot}} \times 100$$

The test results are as shown in Table 2 below.

Table 2

| Compound | Concentration (ppm) | Percentage of Healthy Seedlings (%) | Phytotoxicity |
|---|---|---|---|
| (1) | 500 | 100.0 | — |
| (2) | 500 | 89.3 | — |
| (3) | 500 | 86.7 | — |
| (4) | 500 | 94.7 | — |
| (5) | 500 | 92.7 | — |
| (6) | 500 | 88.0 | — |
| (7) | 500 | 93.3 | — |
| (8) | 500 | 88.0 | — |
| (9) | 500 | 96.7 | — |
| (10) | 500 | 91.3 | — |
| (11) | 500 | 89.4 | — |
| (12) | 500 | 96.7 | — |
| (13) | 500 | 98.0 | — |
| (14) | 500 | 99.3 | — |
| Structure (1): C₆H₅–N(CH₂CN)(COCH₂Cl) | 500 | 16.7 | + |
| Structure (2): 2,4-Cl₂C₆H₃–N(CH₂CN)(COCCl₃) | 500 | 22.0 | + |
| Structure (3): Benzimidazole with CONHC₄H₉(n) and NHCOOCH₃ | 500 | 83.4 | — |
| Inoculated and Untreated Plot | — | 0.0 | — |
| Uninoculated and Untreated Plot | — | 100.0 | — |

The symbol (—) means not phytotoxic and (+) means phytotoxic, hereinafter the same.
Note:
(1), (2) Control (Japanese Pat. Publication No. 1433/1971)
(3) Commercially available fungicide It can clearly be seen from the results shown above that the present compounds have a markedly higher protective activity than the well-known, similar compounds and commercially available fungicides used as a control.

TEST EXAMPLE 2

Protective Activity on Rice Blast (*Pyricularia oryzae*)

When rice plants (var.: Kinki No. 33) had grown to a 4-leave stage in a flower pot of a diameter of 9 cm, an aqueous solution of each emulsifiable concentrate of compounds of the present invention was sprayed thereon at a rate of 10ml per pot. One day later, a spore suspension of *Pyricularia oryzae* was inoculated by spraying, and after 5 more days the number of spots generated on leaves was counted to check the protective activity.

The test results obtained are shown in Table 3.

Table 3

| Compound | Concentration (ppm) | Number of Spots per Leaf | Phytotoxicity |
|---|---|---|---|
| (1) | 500 | 2.3 | — |
| (2) | 500 | 4.6 | — |
| (3) | 500 | 18.4 | — |
| (4) | 500 | 8.7 | — |
| (5) | 500 | 10.6 | — |
| (6) | 500 | 15.7 | — |
| (7) | 500 | 6.3 | — |
| (8) | 500 | 15.7 | — |
| (9) | 500 | 6.1 | — |
| (10) | 500 | 10.6 | — |
| (11) | 500 | 12.3 | — |
| (12) | 500 | 7.7 | — |
| (13) | 500 | 5.6 | — |
| (14) | 500 | 9.2 | — |
| Structure (1): C₆H₅–N(CH₂CN)(COCH₂Cl) | 500 | 50.3 | + |

Table 3-continued

| Compound | Concentration (ppm) | Number of Spots per Leaf | Phytotoxicity |
|---|---|---|---|
| Cl-C₆H₃(Cl)-N(CH₂CN)(COCCl₃) (2) | 500 | 42.8 | + |
| Inoculated and Untreated Plot | — | 58.2 | — |

Note:
(1), (2) Control (Japanese Patent Publication No. 1433/1971)

As can clearly be seen from the test results shown in Table 3 above the compounds of the present invention have a higher protective activity than the control compounds.

TEST EXAMPLE 3

**Protective Activity on Powdery Mildew of the Cucumber (*Sphaerotheca fuliginea*)**

When cucumber (var. Kaga Aonaga-fushinari) had grown, in a flower pot of a diameter of 9 cm, to the beginning of the first true-leaf stage, the leaf was picked, and an aqueous solution of each wettable powder of compounds of the present invention was sprayed on the cotyledon at a rate of 10 ml per pot. One day later, the leaf was inoculated with a spore suspension of *Sphaerotheca fuliginea* by spraying, and after 14 more days, the disease severity was examined. The disease severity was calculated in the following manner. The percentage of the infected leaf area to the total area of the leaf was first obtained and the result classified into six disease ratings ranging from 0 to 5 as follows.

| Disease Rating | Disease Severity Percentage of Infected Leaf Area (%) |
|---|---|
| 0 | No colony on leaf surface |
| 1 | Less than 2 |
| 2 | Less than 30 |
| 3 | Less than 60 |
| 4 | Less than 95 |
| 5 | More than 95 |

Then, the number of the leaves corresponding to each disease rating was counted, from which the disease severity was calculated according to the following relationship.

$$\text{Disease Severity} = \frac{(\Sigma \text{Disease Rating} \times \text{Number of Leaves})}{5 \times \text{Total Number of Leaves}} \times 100$$

The test results obtained are as shown in Table 4.

Table 4

| Compound | Concentration (ppm) | Disease Severity | Phytotoxicity |
|---|---|---|---|
| (1) | 500 | 1.7 | — |
| (2) | 500 | 11.7 | — |
| (3) | 500 | 25.0 | — |
| (4) | 500 | 5.0 | — |
| (5) | 500 | 3.3 | — |
| (6) | 500 | 16.7 | — |
| (7) | 500 | 13.3 | — |
| (8) | 500 | 16.7 | — |
| (9) | 500 | 8.3 | — |
| (10) | 500 | 11.7 | — |
| (11) | 500 | 13.3 | — |
| (12) | 500 | 5.0 | — |
| (13) | 500 | 3.3 | — |
| (14) | 500 | 5.0 | — |
| C₆H₅-N(CH₂CN)(COCH₂Cl) (1) | 500 | 96.7 | + |
| Cl-C₆H₃(Cl)-N(CH₂CN)(COCCl₃) (2) | 500 | 81.7 | + |
| Inoculated and Untreated Plot | — | 100.0 | — |

Note:
(1), (2) Control (Japanese Patent Publication No. 1433/1971)

It can clearly be seen from the results in Table 4 above that the compounds of the present invention have a markedly higher protective activity than the control compounds.

TEST EXAMPLE 4

**Protective Activity on Black Spot of the Pear (*Alternaria kikuchiana*)**

An aqueous solution of each wettable powder of the present invention was sprayed on pear shoots (var.: 20-Seiki) at a rate of 30 mg per shoot. One day later, new leaves were picked, inoculated with spores of *Alternaria kikuchiana* and then placed in a greenhouse. After 7 more days, the disease severity was checked.
The test results are as shown in Table 5.

Table 5

| Compound | Concentration (ppm) | Number of Spots per Leaf | Phytotoxicity |
| --- | --- | --- | --- |
| (1) | 500 | 1.2 | — |
| (2) | 500 | 10.9 | — |
| (3) | 500 | 24.7 | — |
| (4) | 500 | 8.9 | — |
| (5) | 500 | 6.2 | — |
| (6) | 500 | 12.8 | — |
| (7) | 500 | 16.4 | — |
| (8) | 500 | 20.5 | — |
| (9) | 500 | 7.6 | — |
| (10) | 500 | 15.6 | — |
| (11) | 500 | 13.7 | — |
| (12) | 500 | 8.8 | — |
| (13) | 500 | 5.6 | — |
| (14) | 500 | 2.7 | — |
| 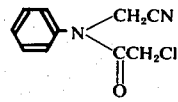 (1') | 500 | 81.4 | + |
| 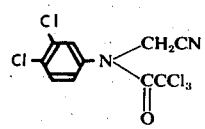 (2') | 500 | 73.8 | + |
| Inoculated and Untreated Plot | — | 84.8 | — |

Note:
(1'), (2') Control (Japanese Patent Publication No. 1433/1971)

As can clearly be seen from the results in Table 5 above the compounds of the present invention have a higher protective activity than that of the control compounds.

TEST EXAMPLE 5

Protective Activity on Stem Rot of the Kidney Bean (*Sclerotinia sclerotiorum*) using Fumigation When kidney beans (ver.: Taisho-kintoki) had grown, in a flower pot of a diameter of 9 cm, to the first true-leaf stage, they were placed, at a rate of five pots per plot, in a chamber tightly enclosed with a vinyl-sheet, and then fumigated for 15 hours with compounds of the present invention at a rate of 100 mg of active ingredient per m³. The sheet was removed, and the leaves were inoculated with *Sclerotinia sclerotiorum* 17 hours after the fumigation treatment. After 4 days, the disease severity was checked in the following manner. The percentage of the infected leaf area to the total area of the leaf was first obtained and the result classified into the six disease ratings ranging from 0 to 5 as follows.

| Disease Rating | Disease Severity Percentage of Infected Leaf Area (%) |
| --- | --- |
| 0 | 0 |
| 1 | Slight infection around the inoculum |
| 2 | Less than 20 |
| 3 | Less than 40 |
| 4 | Less than 60 |
| 5 | More than 60 |

Then, the numbers of leaves, $n_0$ to $n_5$, corresponding to respective disease rating were counted, from which the disease severity was calculated according to the following relationship.

$$\text{Disease Severity} = \frac{0 \times n_0 + 1 \times n_1 + \cdots + 5 \times n_5}{5 \times n} \times 100$$

The test results obtained are as shown in Table 6.

Table 6

| Compounds | Amount Applied (mg/m³) | Disease Severity | Phytotoxicity |
| --- | --- | --- | --- |
| (1) | 100 | 3.3 | — |
| (2) | 100 | 8.3 | — |
| (3) | 100 | 16.7 | — |
| (4) | 100 | 11.7 | — |
| (5) | 100 | 5.0 | — |
| (6) | 100 | 6.7 | — |
| (7) | 100 | 13.3 | — |
| (8) | 100 | 13.3 | — |
| (9) | 100 | 11.7 | — |
| (10) | 100 | 8.3 | — |
| (11) | 100 | 11.7 | — |
| (12) | 100 | 3.3 | — |
| (13) | 100 | 5.0 | — |
| (14) | 100 | 6.7 | — |
| 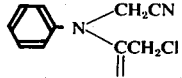 (1') | 100 | 88.3 | + |
| 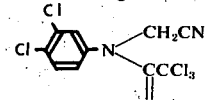 (2') | 100 | 95.0 | + |
| Inoculated and Untreated Plot | — | 100.0 | — |

Note:
(1'), (2') Control (Japanese Patent Publication No. 1433/1971)

It can be seen from the results set forth above that the compounds of the present invention have a higher protective activity than that of the control compounds.

TEST EXAMPLE 6

Protective Activity Test Using White Water

Ten grams of each of Compounds (1) to (22) of the invention were dissolved in 100 ml of water, and 5 ml of each solution was diluted with 1 liter of the white water resulting from a groundwood-pulp production process. Five ml of each resulting solution was further diluted with 2 liters of white water. To 100 ml of the test solution thus obtained were added 10g of grape sugar, 1g of peptone, 0.05g of magnesium sulfate and 0.01g of calcium chloride, and the mixture was sterilized by heating and inoculated with *Bacillus, sp.* alone which was isolated from the slime resulting from a paper-making process. Propagation of the fungus was not observed, on the other hand, a vigorous propagation was observed in an untreated sample within 24 hours.

It is clear from the above test examples that the compounds of formula (I) of the present invention have a markedly higher fungicidal activity than that of their homologues and thus can contribute greatly to an increase in agricultural production.

While the invention has been described in detail and with reference to specific embodiments thereof, it will be apparent to one skilled in the art that various changes and modifications can be made therein without departing from the spirit and scope thereof.

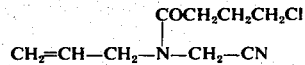

What is claimed is:

1. A compound